(12) United States Patent
Heck et al.

(10) Patent No.: US 8,051,715 B2
(45) Date of Patent: Nov. 8, 2011

(54) RESONANT INSPECTION USING RECONFIGURABLE NEST

(75) Inventors: David P. Heck, St. Charles, MO (US); Adrian P. Allen, Doncaster (GB)

(73) Assignee: The Boeing Company, Chicago, IL (US)

( * ) Notice: Subject to any disclaimer, the term of this patent is extended or adjusted under 35 U.S.C. 154(b) by 507 days.

(21) Appl. No.: 12/392,702

(22) Filed: Feb. 25, 2009

(65) Prior Publication Data
US 2010/0212427 A1  Aug. 26, 2010

(51) Int. Cl.
*G01N 29/12* (2006.01)
(52) U.S. Cl. ............................. 73/579; 73/618
(58) Field of Classification Search .............. 73/579, 73/602, 618, 659
See application file for complete search history.

(56) References Cited

U.S. PATENT DOCUMENTS

| | | | | |
|---|---|---|---|---|
| 3,662,589 | A * | 5/1972 | Adler et al. ...................... | 73/602 |
| 4,307,614 | A * | 12/1981 | Tittmann et al. ................ | 73/629 |
| 5,062,296 | A * | 11/1991 | Migliori .......................... | 73/579 |
| 5,228,004 | A * | 7/1993 | Kawasaki ........................ | 367/13 |
| 5,351,543 | A * | 10/1994 | Migliori et al. ................. | 73/579 |
| 5,355,731 | A * | 10/1994 | Dixon et al. .................... | 73/579 |
| 5,490,436 | A * | 2/1996 | Coyne et al. .................. | 464/180 |
| 5,631,423 | A | 5/1997 | Rhodes ........................... | 73/579 |
| 5,837,896 | A * | 11/1998 | Rhodes et al. .................. | 73/579 |
| 5,992,234 | A | 11/1999 | Rhodes et al. .................. | 73/579 |
| 6,330,827 | B1 * | 12/2001 | Johnson et al. ................. | 73/579 |
| 6,647,611 | B2 * | 11/2003 | Zhang ............................. | 29/559 |
| 2001/0050454 | A1 * | 12/2001 | Zhang .............................. | 269/7 |
| 2002/0114424 | A1 * | 8/2002 | Kroener et al. ................. | 378/4 |
| 2007/0041488 | A1 * | 2/2007 | Hoheisel et al. ................ | 378/4 |

OTHER PUBLICATIONS

"Quasar Process Compensated Resonant Testing: Principles of Operation", Quasar International, Inc., 10 pgs, 2006.

* cited by examiner

*Primary Examiner* — Freddie Kirkland, III
(74) *Attorney, Agent, or Firm* — Caven & Aghevli LLC

(57) ABSTRACT

The present disclosure provides a device and method for non-destructive testing of an object using resonant ultrasound spectroscopy, wherein the device is provided with a reconfigurable nest for placement of objects of various shapes and sizes on the device. The reconfigurable nest includes a plurality of transducers that are held in place using a rheological fluid. As each transducer is arranged, for example, using a robotic tool, an electric or magnetic field is applied to the rheological fluid in contact with said transducer, thereby holding the transducer in place. This device and method thus provide a nest for a resonant inspection device that may be reconfigured in much less time and with much less effort when compared to existing solutions.

20 Claims, 3 Drawing Sheets

# US 8,051,715 B2

RESONANT INSPECTION USING RECONFIGURABLE NEST

FIELD

The present disclosure is generally related to nondestructive testing, and more particularly, to an apparatus and method for measuring ultrasonic vibrations at a natural frequency of an object to determine the structural integrity of the object.

BACKGROUND

Resonant Ultrasound Spectroscopy (RUS) describes the application of acoustic waves to mechanical structures in order to detect small defects. The frequencies of the acoustic waves are varied across the frequency range of interest by defining a response time interval, dependent upon the elastic properties of the material, and a frequency step interval, wherein the acoustic wave frequency is varied at intervals across a range of interest and measured over a predetermined response time interval. The structure vibrates when the drive matches the frequency of one of its characteristic modes. Higher order modes are targeted so that very small defects can be detected.

Referring to FIG. 1, performing RUS involves generating a signal with a signal generator 14, emitting the acoustic wave signal onto an object or part 12 with a drive transducer 16, detecting the vibration of the object with at least one receiving transducer 18, processing the output signal with amplifier 22, and analyzing the signal with computer 24.

The object is supported typically by three piezoelectric transducers, one for emitting the acoustic wave signal and at least one of the other two transducers for measuring the response. Obtaining reliable resonant data over a range of frequencies requires reliable part placement on the test station, as well as temperature compensation and sophisticated data analysis. In order to achieve reliability, the testing apparatus must be configured for each specific part. This includes a custom arrangement of the piezoelectric transducers as well as support pins or other structures for holding a particular part in place. The arrangement of positioning posts and piezoelectric transducers must be maintained at a predetermined spacing in order to provide accurate results. When the apparatus is reconfigured for a different part, the transducers and positioning posts must be relocated and fastened in place.

Reconfiguring the apparatus for different parts can be time-consuming and is particularly costly for industries where the number of each type of part is relatively low. For this reason, there is a need for a method and apparatus for conducting resonant inspection that reduces the costs associated with reconfiguration of the piezoelectric transducer and/or positioning post arrangement.

SUMMARY

The present disclosure addresses the needs of the industry by providing a device and method for non-destructive testing of a object using resonant ultrasound spectroscopy, wherein the device is provided with a reconfigurable nest for placement of objects of various shapes and sizes on the device. The reconfigurable nest includes a plurality of transducers that are held in place using a rheological fluid. As each transducer is arranged, for example, using a robotic tool, an electric or magnetic field is applied to the rheological fluid in contact with said transducer, thereby holding the transducer in place. This device and method thus provide a nest for a resonant inspection device that may be reconfigured in much less time and with much less effort when compared to existing solutions.

One aspect of the present disclosure provides a device for inspection of an object using resonant ultrasound spectrometry. The device includes a signal generator for generating an ultrasound test signal; a drive transducer for transferring the ultrasound test signal onto the object; at least one receiving transducer for detecting the vibration of the object caused by the ultrasound test signal; and a container filled with rheological fluid that holds the drive and receiving transducers in place.

Another aspect of the present disclosure provides a method for inspection of an object using resonant ultrasound spectrometry. A drive transducer and at least one receiving transducer are arranged in a desired configuration for the inspection of the object and the transducers are placed in contact with a rheological fluid. The viscosity of the rheological fluid is increased by activating at least one electrode in contact with the rheological fluid to hold the transducers in place. The object is then placed in contact with the drive transducer and the at least one receiving transducer. An ultrasound test signal is generated and applied to the object using the drive transducer causing the object to vibrate. The vibration is then detected using the receiving transducer.

Other systems, methods, features, and advantages of the present disclosure will be or become apparent to one with skill in the art upon examination of the following drawings and detailed description. The features, functions and advantages that have been discussed can be achieved independently in various embodiments of the present disclosure or may be combined in yet other embodiments further details of which can be seen with reference to the following description and drawings.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

The present disclosure provides a device for non-destructive testing of a object that may be reconfigured quickly and easily for various types of objects. The device and method of the present disclosure are useful for finding small defects in objects such as parts or devices made of metal, ceramics, or any other material that responds to any wavelength of an acoustic wave signal.

The device and method of the present disclosure use rheologic fluid to hold the transducers of the device in place. A rheological fluid is a "smart fluid" whose viscosity can be changed by application of an electric or magnetic field. The most common rheological fluids are magnetorheological fluids that comprise a suspension of very small magnetic particles in a carrier fluid, usually a type of oil. When a magnetic field is applied to a magnetorheological fluid, the viscosity may be increased to the point of becoming a viscoelastic solid. By varying the intensity of the magnetic field, the yield stress of the fluid may be controlled with great accuracy. Electrorheological fluids are similar to magnetorheological fluids, except that the magnetic particles are replaced with non-conducting particles. Electrorheological fluids are not typically capable of achieving the viscoelastic solid-like state useful for this application. Ferrofluids or other smart fluids also are considered viable alternatives.

As discussed above, different objects will usually require different configurations of transducers and/or support pins to hold the object in place and acquire the desired response. In circumstances where several different parts require testing using the same device, the present disclosure will drastically reduce the amount of down-time that would be spent reconfiguring the nest where the device is placed.

Figure 1:
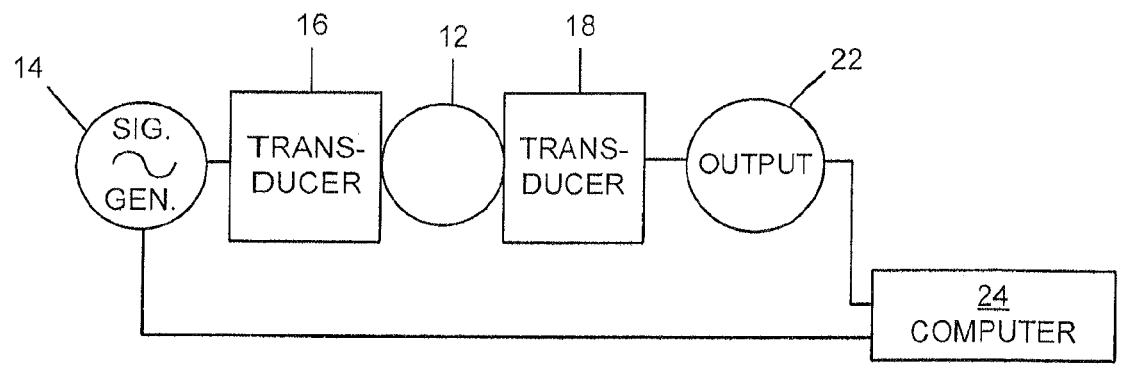
FIG. 1 is a schematic of a resonant inspection device.
Figure 2:
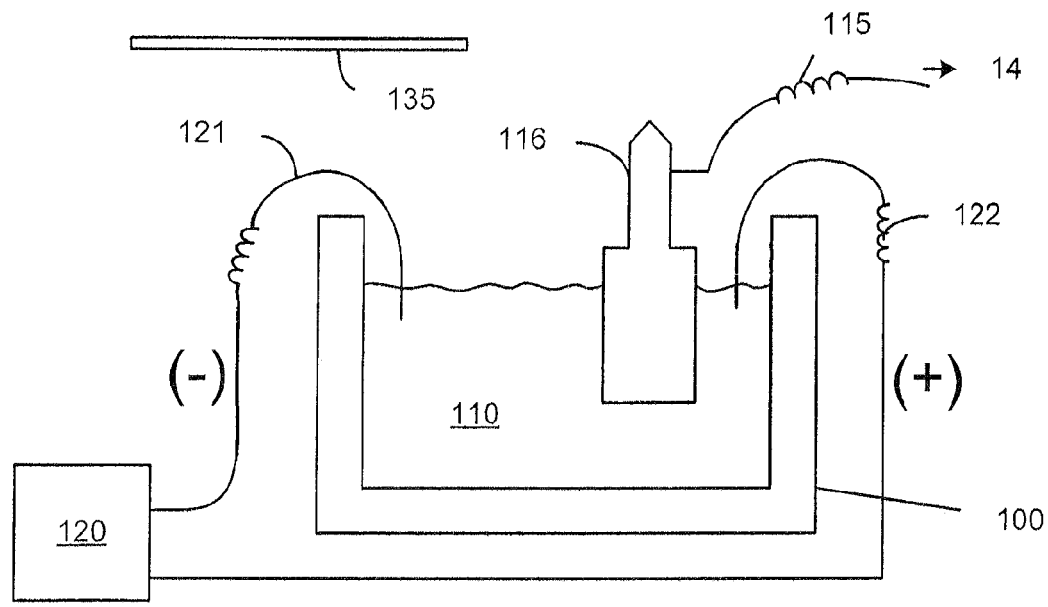
FIG. 2 is a sectioned side view of a portion of a reconfigurable nest for resonant inspection in accordance with the present disclosure.
Figure 3:
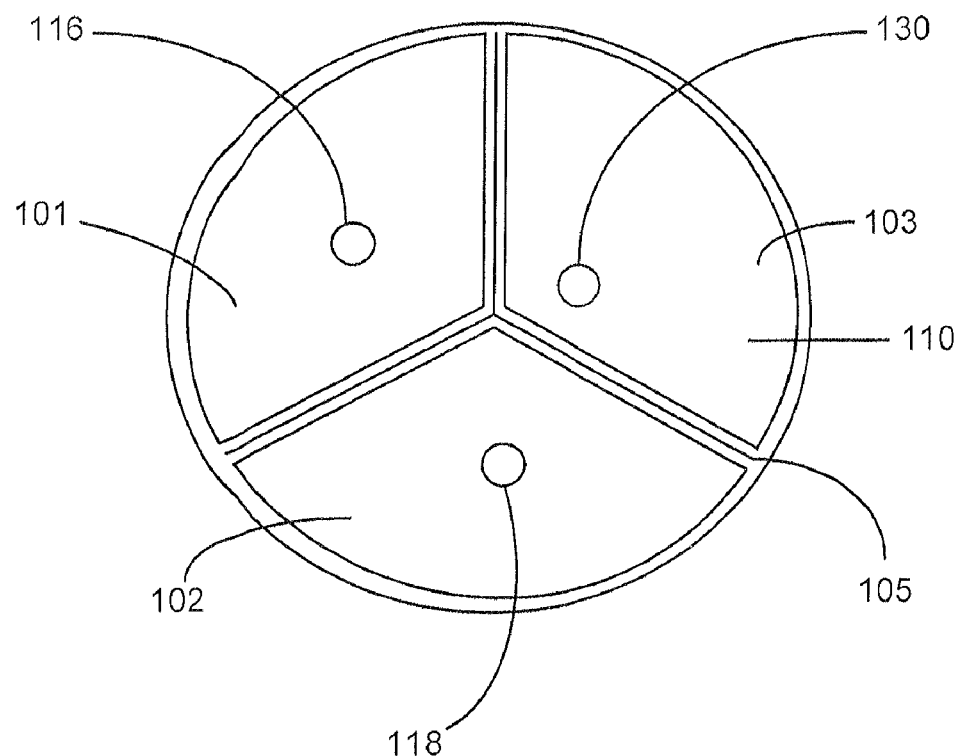
FIG. 3 is a top view of a reconfigurable nest for resonant inspection in accordance with the present disclosure.
Figure 4:
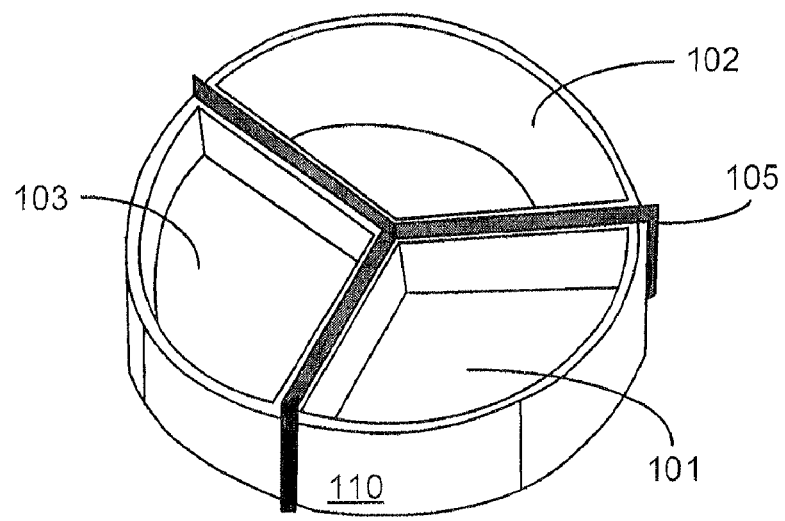
FIG. 4 is an illustration of a 3-bay rheological fluid container in accordance with the present disclosure.

One aspect of the present disclosure provides a device for resonant inspection of an object in accordance with the schematic of FIG. 1, and employing a container filled with rheological fluid for holding the transducers or support pins in place. Referring to FIGS. 2-4, the container holds the rheological fluid 110 which is in contact with a drive transducer 116, at least one receiving transducer 118, and may also be in contact with at least one support pin 130. The rheological fluid is contacted by at least one electrode 121, 122 through which an electric or magnetic field may be applied to the rheological fluid, thereby increasing its viscosity. The electric or magnetic field is chosen according the rheologic fluid and should be sufficient to hold the transducers and/or support pins in place so that accurate measurements are received. For this purpose, negative and positive electrodes 121, 122, respectively, are connected to a device 120 for generating the optimal electric or magnetic field.

In one embodiment, the transducers and/or support pins may be in contact with the same volume of rheological fluid. However, as shown in FIGS. 3 and 4, the container also may be divided into three bays containing separated volumes of rheological fluid. The bays may be separated by an insulating material 105. The rheological fluid in each bay is contacted by at least one electrode. The desired electric or magnetic field may be applied to each bay separately.

FIGS. 3 and 4 show the container having three bays 101, 102, 103 in a pie-shaped configuration, however, many other arrangements also are possible. For example, the container may resemble a series of boxes or containers lined end to end. The figure shows three bays because providing three points of contact for the object is a simple and generally stable configuration. However, additional bays may also be used if the desired application uses additional support pins, which for purposes of this disclosure necessarily includes other support objects that may not resemble pins.

With the container divided into a plurality of bays, each bay may be used to hold a single transducer or support pin. In this manner, each transducer or support pin may be locked into place individually. The robotic tool may then move each transducer or support pin individually by deactivating the electrodes in one bay while the remaining electrodes remain active, moving the transducer or support pin within said bay, and reactivating the electrodes in said bay to lock the transducer or support pin in place. Alternatively, the transducers or support pins may be moved to another bay or replaced with different support pins by the robotic tool. This may be accomplished by deactivating all electrodes, moving the transducers or support pins with the robotic tool, and activating the appropriate electrodes as the transducers or support pins are placed in position.

Other alternative methods of placement are possible. For example, the robotic tool may be capable of moving multiple pieces simultaneously. In this instance, the container of rheological fluid may provide the desired function without being divided into a plurality of bays. Another alternative would be to have one support pin or transducer in a fixed position while the other transducers or support pins move relative to the transducer or support pin in a fixed position. Additionally, it may be possible to rearrange the bays of the rheological fluid container if the desired configuration for two objects varies greatly. Many other alternatives are possible and all are considered within the scope of the present disclosure.

The transducers employed in the present disclosure are typically piezoelectric transducers, though electrostatic transducers also may be used. The drive transducer receives the acoustic wave signal from the signal generator and transfers this energy to the object to be tested, causing it to vibrate. At least one receiving transducer is used to detect the vibrations of the object. This signal is then processed and analyzed using known RUS techniques to determine if the object has any defects.

The transducers and/or support pins may be arranged using a robotic tool 135. The robotic tool may be programmed with the location and orientation of each transducer and/or support pin for each part. When the transducer and/or support pin has been properly arranged, the magnetic or electric field is applied to the rheological fluid, locking the transducer or support pin in place. During the arrangement of the support pin, the support pin may be replaced with a different sized support pin, including any other support structure required for a specific object.

Figure 5:
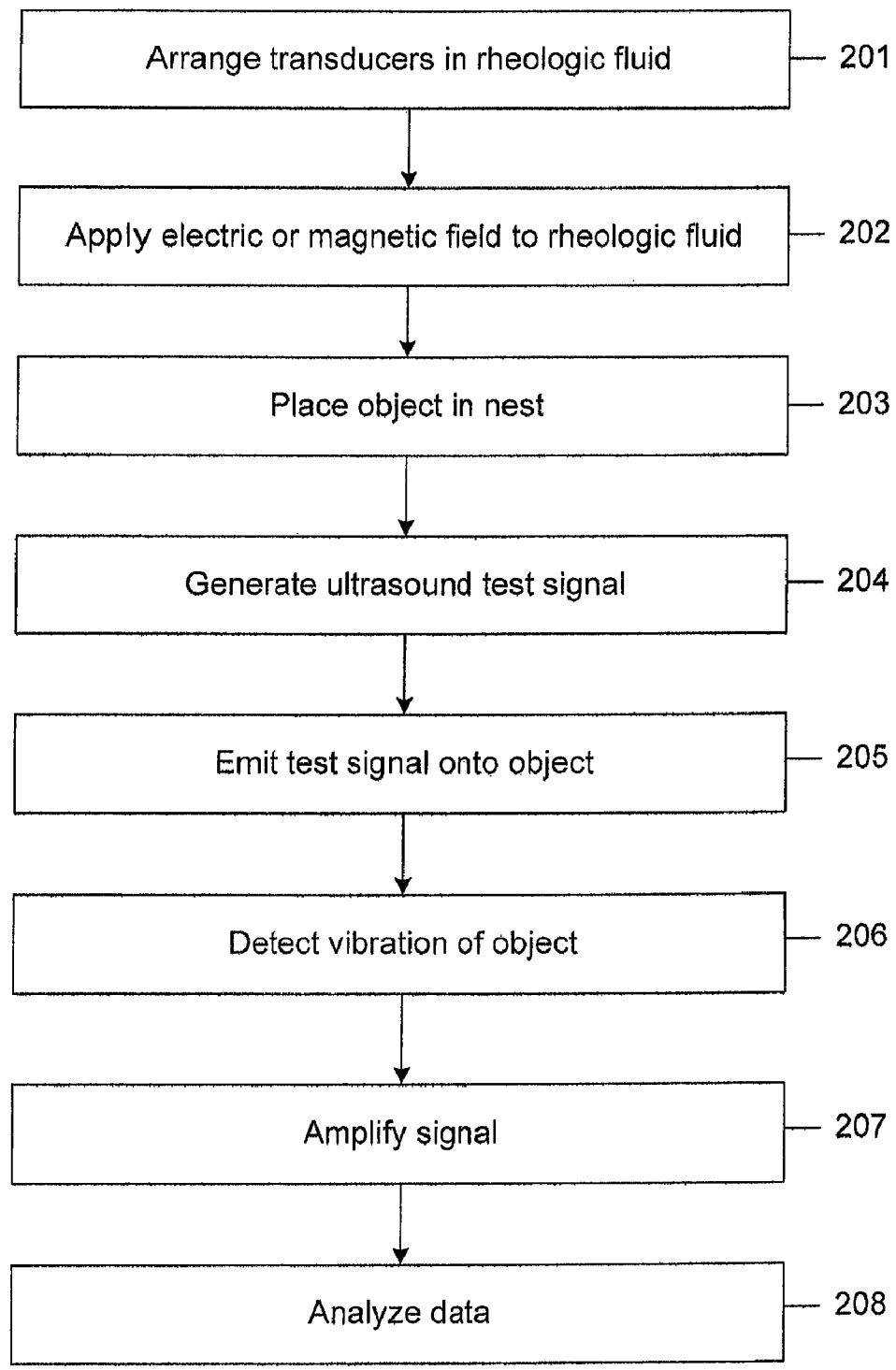
FIG. 5 is a flowchart illustrating a method of performing resonant inspection with a reconfigurable nest, in accordance with the present disclosure.

Referring to FIG. 5, another aspect of the present disclosure provides a method for inspection of an object using RUS wherein the device may be easily reconfigured. The method of the present disclosure includes arranging a drive transducer and at least one receiving transducer in a rheological fluid 201. A magnetic or electric field is applied to the rheological fluid to "lock" the transducers in place 202. The object is then placed in the nest 203, the nest comprising the arrangement of transducers and support pins. Once the object has been placed, an ultrasound test signal is generated 204 and emitted onto the object 205. The vibration of the object is then measured using a receiving transducer 206, the signal from the receiving transducer being amplified 207 and sent to a computer for analyzing 208.

The arrangement of the transducers may be optimized for the object to be tested. Alternatively, the arrangement for a particular object may also include one or more support pins, which for purposes of this disclosure necessarily includes other support objects that may not resemble pins.

A robotic tool may be used to place the transducers and/or support pins. The robotic tool can place the transducers and/or support pins according detailed coordinates supplying information regarding placement and orientation. In addition, the robotic tool may be used to place the object to be tested in the nest. Where desired, the robotic tool may include several appendages for arranging multiple pieces simultaneously.

Several algorithms for analyzing the data received from the receiving transducer are known in the art. The data is compared with expected results and with the results from tests on similar objects. All of these methods are compatible with the present disclosure are considered included herein.

It should be emphasized that the above-described embodiments of the present disclosure, particularly, any "preferred" embodiments, are merely possible examples of implementations, merely set forth for a clear understanding of the principles of the present disclosure. Many variations and modifications may be made to the above-described embodiments without departing substantially from the spirit and principles of the disclosure. All such modifications and variations are intended to be included herein within the scope of this disclosure and protected by the following claims.

What is claimed is:

1. A device for inspection of an object using resonant ultrasound spectrometry, comprising:
    a signal generator for generating an ultrasound test signal;
    a drive transducer electrically connected to the signal generator for emitting the ultrasound test signal onto the object;
    at least one receiving transducer for detecting the vibration of the object caused by the ultrasound test signal; and
    a container containing a rheological fluid for holding the drive and receiving transducers in place.

2. The device of claim 1, wherein the rheological fluid and the container are used to hold the drive and receiving transducers in a desired configuration chosen for the object to be inspected.

3. The device of claim 2, further comprising a robotic tool for moving the transducers to a desired configuration.

4. The device of claim 1, further comprising one or more electrodes in contact with the rheological fluid.

5. The device of claim 1, further comprising at least one support pin for holding the object in a desired position.

6. The device of claim 1, wherein the container comprises a plurality of bays separating the rheological fluid, wherein no more than one transducer is placed in a single bay.

7. The device of claim 6, wherein the container is comprised of three bays, each of which contains a volume of rheological fluid, and wherein the drive transducer is located in a first bay, the receiving transducer is located in a second bay, and a support pin or a dormant transducer is located in a third bay.

8. The device of claim 6, comprising a plurality of electrodes, at least one electrode connected to the rheological fluid in each bay.

9. The device of claim 1, wherein the viscosity of the rheological fluid is increased by the application of an electric or magnetic field.

10. The device of claim 1, further comprising an amplifier and a computer, wherein the signal from the at least one receiving transducer is transmitted to the computer through the amplifier.

11. The device of claim 1, wherein the ultrasound test signal is generated to emit a series of acoustic wave signals over a predetermined frequency range.

12. The device of claim 1, wherein at least one of the transducers is fixed in position.

13. A method for inspection of a object using resonant ultrasound spectrometry, comprising:
    arranging a drive transducer and at least one receiving transducer in a desired configuration for inspection of the object, wherein the drive transducer and the at least one receiving transducer are in contact with a rheological fluid;
    modifying the viscosity of the rheological fluid by activating at least one electrode in contact with the rheological fluid;
    placing the object in contact with the drive transducer and the at least one receiving transducer;
    generating an ultrasound test signal;
    emitting the ultrasound test signal onto the object to cause vibration using the drive transducer; and
    detecting vibration of the object using the at least one receiving transducer.

14. The method of claim 13, wherein the transducers are arranged using a robotic tool.

15. The method of claim 14, wherein the robotic tool is used to arrange at least one support pin in the rheological fluid.

16. The method of claim 13, wherein the rheological fluid is separated into three bays, and wherein the drive transducer is located in a first bay, the receiving transducer is located in a second bay, and a support pin or a dormant transducer is located in a third bay.

17. The method of claim 16, wherein at least one electrode is connected to the rheological fluid in each bay, and wherein the at least one electrode connected to each bay is activated as the transducer or support pin located in said bay is put in place using a robotic tool.

18. The method of claim 13, wherein a viscosity of the rheological fluid is modified by the application of an electric or magnetic field.

19. The method of claim 13, further comprising amplifying the signal detected by the receiving transducer and transmitting the amplified signal to a computer and analyzing the signal using the computer.

20. The method of claim 13, wherein the ultrasound test signal is comprised of a series of acoustic wave signals varied at a step interval over a predetermined frequency range.

\* \* \* \* \*